United States Patent
Schwab et al.

[11] Patent Number: 6,020,372
[45] Date of Patent: Feb. 1, 2000

[54] USE OF ISOXAZOLE AND CROTONAMIDE DERIVATIVES FOR THE TREATMENT OF CARCINOMATOUS DISORDERS

[75] Inventors: Wilfried Schwab, Wiesbaden; Jörg Czech; Klaus Boslett, both of Marburg, all of Germany

[73] Assignee: Hoechst Aktiengesellschaft, Frankfurt am Main, Germany

[21] Appl. No.: 09/191,375

[22] Filed: Nov. 13, 1998

Related U.S. Application Data

[63] Continuation of application No. 08/733,050, Oct. 16, 1996, Pat. No. 5,886,033.

[30] Foreign Application Priority Data

Oct. 25, 1995 [DE] Germany ............ 195 39 638

[51] Int. Cl.⁷ .................................. A61K 31/275
[52] U.S. Cl. .................. 514/521; 514/572; 558/392; 558/393
[58] Field of Search ............ 514/521, 572; 558/392, 393

[56] References Cited

U.S. PATENT DOCUMENTS

| | | | |
|---|---|---|---|
| 4,061,767 | 12/1977 | Ertel et al. | 424/282 |
| 5,476,866 | 12/1995 | Kuo et al. | 514/378 |
| 5,494,911 | 2/1996 | Bartlett et al. | 514/256 |

FOREIGN PATENT DOCUMENTS

| | | |
|---|---|---|
| 0 013 376 | 7/1980 | European Pat. Off. . |
| 0 484 223 | 5/1992 | European Pat. Off. . |
| 0 538 783 | 4/1993 | European Pat. Off. . |
| 0 551 230 | 7/1993 | European Pat. Off. . |
| 0 665 013 | 8/1995 | European Pat. Off. . |
| WO 95/19169 | 7/1995 | WIPO . |

OTHER PUBLICATIONS

S. Chen et al., Cancer Research, vol. 52, pp. 3521–3527 (1992).

R. Hay et al., American Type Culture Collection Catalogue of Cell Lines and Hybridomas, Sixth Ed. (1988), pp. 168, 157, 120, 126, 127.

G. J. Peters et al., Biochemical Pharmacology, vol. 39, No. 1, pp. 135–144 (1990).

G. Schwartsmann et al., Biochemical Pharmacology, vol. 37, No. 1, pp. 3257–3266 (1988).

G.J. Peters et al., Invest. New Drugs, vol. 5, pp. 235–244 (1987).

G.J. Peters et al., Proceedings of AACR, vol. 27, pp. 350, 1392 (Mar., 1988).

R. A. Williamson et al., J. of Biological Chemistry, vol. 270, No. 88, pp. 22467–22472 (Sep. 22, 1995).

*Primary Examiner*—Peter O'Sullivan
*Attorney, Agent, or Firm*—Finnegan, Henderson, Farabow, Garrett & Dunner, L.L.P.

[57] ABSTRACT

The compound of the formula I or II

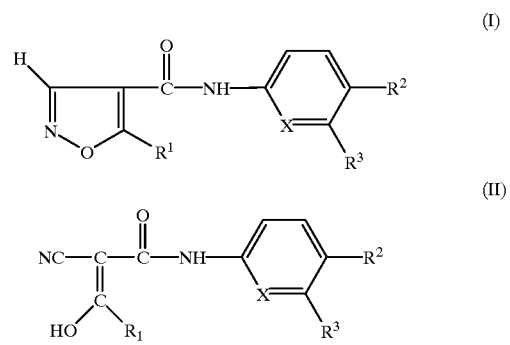

is suitable for the production of a pharmaceutical for the treatment of carcinomatous disorders, where $R^1$ is $(C_3-C_5)$-cycloalkyl, $(C_2-C_6)$-alkenyl or $(C_2-C_6)$-alkynyl, $R^2$ is $CF_3$, $OCF_3$, $SCF_3$, $OH$, $NO_2$, halogen, benzyl, phenyl, CN or O-phenyl, $R^3$ is $(C_1-C_4)$-alkyl, halogen or a hydrogen atom and X is a —CH group or a nitrogen atom.

4 Claims, No Drawings

USE OF ISOXAZOLE AND CROTONAMIDE DERIVATIVES FOR THE TREATMENT OF CARCINOMATOUS DISORDERS

This is a continuation of application U.S. Ser. No. 08/733,050, filed Oct. 16, 1996, now U.S. Pat. No. 5,886,033, which is incorporated herein by reference.

DESCRIPTION

Chemotherapy is today available for the therapy of advanced hormone receptor-negative malignant tumors. Beside its limited efficiency, this form of therapy is characterized by the occurrence of often serious side effects. The active principle of the chemotherapeutics (inhibition of proliferation) must be regarded as a cause of the action and the side effects. Since, however, not only tumor cells, but also normal cells are in division, normal dividing cells in the body of the patient are inhibited from division just like the actual target cells, the tumor cells. The rapidly dividing cells of the hair follicles, of the gastrointestinal tract and of the bone marrow are particularly affected by the undesired side effects of the antiproliferative therapy.

The antiproliferative action of the chemotherapeutics is achieved, for example, by them intervening in the nucleic acid metabolism of the cell. Particularly effective antiproliferative substances are the dihydroorotate dehydrogenase (DHODH) inhibitors. DHODH is a unique enzyme in the de novo synthesis of the pyrimidine nucleotides (Peters et al., 1990, Biochemical Pharmacology 39: No. 1, 135–144). The enzyme is concentrated on the outside of the inner mitochondrial membrane. Inhibition of the enzyme by the active compound DUP-785 (Brequinar) leads to a depletion of pyrimidine ribo- and deoxyribonucleotides, but not of purine nucleotides (Schwartsmann et al., 1988, Biochem. Pharmacol. 37: 3257–3266). The depletion of dTTP and dCTP is proportional to that of UTP and CTP and can be prevented by the addition of uridine. The inhibition of growth exerted on in vitro cell lines by Brequinar can be abolished by addition of uridine or cytidine, but not by deoxythymidine or deoxycytidine. It can be concluded from this that the inhibition of UMP synthesis is crucial for the proliferation-inhibiting effect on cell lines in vitro (Peters et al., 1987, Invest. New Drugs, 5: 235–244).

In the context of clinical investigations, it was possible to show that Brequinar significantly lowers the plasma uridine values (Peters et al., 1988, Proc. Am Ass. Cancer Res. 29: 350 (Abstract 1392)) (this finding is in agreement with the in vitro observations on various cell lines). In addition, the extent of effects on the in vivo uridine level correlated with the bone marrow and gastrointestinal tract toxicity (the side effects).

These clinical observations point to the fact that there is the urgent need to develop cancer therapeutics whose antitumor principle is not based on a general inhibition of proliferation, such as in the case of Brequinar, but on the inhibition of tumor-specific metabolic pathways.

It has now been found that the compounds of the formulae I and II only very weakly inhibit human DHODH, but very efficiently block very specific tumor cell lines in their division.

Addition of increasing amounts of uridine in the MTT test changes the $IC_{50}$ value of the substances according to the invention on the LoVo cell line only insignificantly, completely in contrast to the massive increase in the $IC_{50}$ value of Brequinar on the same cell line (Example 7).

These experimental findings support the assumption that the antiproliferative action of the substances according to the invention is based on a principle of action other than an inhibition of DHODH as in the case of Brequinar.

It was possible to show by means of fluorescence microscopy techniques that those cell lines which strongly overexpress the PDGF receptor and the VEGF receptor are also efficiently prevented from division (Example 6) by very low concentrations of the substances according to the invention (lower $IC_{50}$). This observation as a result points to the fact that the substances according to the invention could block specific receptor tyrosine kinases, such as, for example, the PDGF receptor, i.e. advantageously affect the abnormal signal transmission in tumor cells.

The invention therefore relates to the use of a compound of the formula I or II

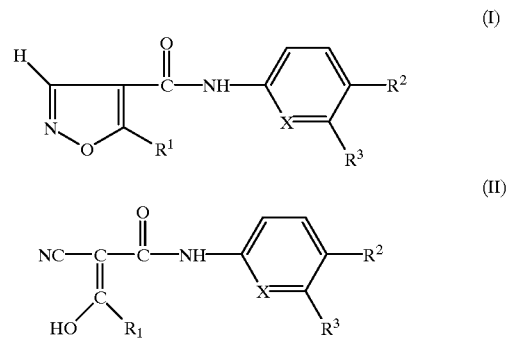

and/or an optionally stereoisomeric form of the compound of the formula I or II and/or a physiologically tolerable salt of the compound of the formula II for the production of a pharmaceutical for the treatment of carcinomatous disorders, where $R^1$ is
 a) $(C_3–C_5)$-cycloalkyl,
 b) $(C_2–C_6)$-alkenyl or
 c) $(C_2–C_6)$-alkynyl, $R^2$ is
 a) —$CF_3$,
 b) —O—$CF_3$,
 c) —S—$CF_3$,
 d) —OH,
 e) —$NO_2$,
 f) halogen,
 g) benzyl,
 h) phenyl,
 i) —CN,
 k) —O—phenyl,
 l) —O—phenyl, mono- or polysubstituted by
  1) $(C_1–C_4)$-alkyl,
  2) halogen,
  3) —O—$CF_3$ or
  4) —O—$CH_3$, $R^3$ is
 a) $(C_1–C_4)$-alkyl,
 b) halogen or
 c) a hydrogen atom, and X is
  a) a —CH group or
  b) a nitrogen atom.

The use is preferred of a compound of the formula I or II and/or an optionally stereoisomeric form of the compound of the formula I or II and/or sodium or lysinium salts of the compound of the formula II, where $R^1$ is cyclopropyl, $(C_2$–$C_3)$-alkenyl or $(C_3$–$C_5)$-alkynyl,
$R^2$ is —O—$CF_3$, —S—$CF_3$, —O—phenyl, phenyl, —$CF_3$, —CN or —O—phenyl, mono- or polysubstituted by $(C_1$–$C_4)$-alkyl or halogen,
$R^3$ is a hydrogen atom or methyl, and
X is a —CH group, for the production of a pharmaceutical for the treatment of carcinomatous disorders.

The use is particularly preferred of a compound of the formula I or II, where $R^1$ is cyclopropyl, $C_3$-alkenyl or $C_4$-alkynyl,
$R^2$ is —S—$CF_3$, CN, 2-methyl-4-chlorophenyl or $CF_3$,
$R^3$ is a hydrogen atom, and
X is a —CH group, for the production of a pharmaceutical for the treatment of carcinomatous disorders.

In particular, the use is preferred of N-(4-trifluoromethylphenyl)-2-cyano-3-hydroxyhexa-2,5-dienecarboxamide, 2-cyano-3-cyclopropyl-3-hydroxyacrylic acid (4-trifluoromethylphenyl)amide, 2-cyano-3-cyclopropyl-3-hydroxyacrylic acid (4-thiotrifluoromethylphenyl)amide, 2-cyano-3-cyclopropyl-3-hydroxyacrylic acid (2-methyl-4-chlorophenyl)amide, N-(4-trifluoromethylphenyl)-2-cyano-3-hydroxy-hept-2-en-6-ynecarboxamide lysine or sodium salt or 2-cyano-3-cyclopropyl-3-hydroxyacrylic acid (4-cyanophenyl)amide lysine or sodium salt.

The compounds of the formula I or II are prepared by known processes such as are described in EP 13 376; EP 484 223; EP 538 783; EP 551 230 or U.S. Pat. No. 4 061 767.

The term alkyl, alkenyl or alkynyl is understood as meaning radicals whose carbon chain can be straight-chain or branched. The alkenyl or alkynyl radicals can furthermore also contain two or more double bonds or two or more triple bonds. Cyclic alkyl radicals are, for example, 3- to 5-membered monocyclic systems such as cyclopropyl, cyclobutyl or cyclopentyl. The starting substances for the chemical reactions are known or can be readily prepared by methods known from the literature. The carcinomatous disorders include, for example, leukemia, in particular chronic leukemia of the T- and B-cell type, Hodgkin's or non-Hodgkin's lymphoma, carcinoma, lung cancer, ovarian cancer, lymph node cancer, sarcoma, Kaposi's sarcoma, meningioma, intestinal cancer, brain tumors, breast cancer, stomach cancer, pancreatic cancer, prostatic cancer or skin cancer.

The invention also relates to a process for the production of a pharmaceutical for the treatment of carcinomatous disorders, which comprises bringing the compound of the formula I or II and/or a physiologically tolerable salt of the compound of the formula II into a suitable administration form using a pharmaceutically suitable and physiologically acceptable excipient and, if appropriate, further suitable active compounds, additives or auxiliaries. The pharmaceuticals according to the invention can be administered orally, topically, rectally, intravenously or alternatively parenterally.

Suitable solid or liquid pharmaceutical administration forms are, for example, granules, powders, coated tablets, tablets, (micro)capsules, suppositories, syrups, juices, suspensions, emulsions, drops or injectable solutions and also preparations having a protracted release of active compound, in whose preparation customary auxiliaries, such as excipients, disintegrants, binders, coating agents, swelling agents, glidants or lubricants, flavorings, sweeteners or solubilizers are used. Frequently used auxiliaries which may be mentioned are, for example, magnesium carbonate, titanium dioxide, lactose, mannitol and other sugars, talc, lactoprotein, gelatin, starch, cellulose and its derivatives, animal and vegetable oils, polyethylene glycols and solvents, such as, for example, sterile water and mono- or polyhydric alcohols, e.g. glycerol.

Preferably, the pharmaceutical preparations are prepared and administered in dose units, each unit as active constituent containing a certain dose of the compound of the formula I or II and/or physiologically tolerable salts of the compound of the formula II. In the case of solid dose units, such as tablets, capsules or suppositories, this dose can be up to approximately 300 mg, but preferably 10 to 200 mg.

As used herein, the term "patient" refers to a warm-blooded animal or mammal which is afflicted with a carcinomatous disorder. It is understood that guinea pigs, dogs, cats, rats, mice, hamsters, rabbits and primates, including humans, are examples of patients within the scope of the meaning of the term.

A "therapeutically effective amount" of a compound of formulae (I) or (II) is an amount which is effective, upon single or multiple dose administration to the patient, in controlling the growth of tumor cells or neoplasms or in prolonging the survivability of the patient beyong that expected in the absence of such treatment. As used herein, "controlling the growth" of the tumor cells or neoplasms refers to slowing, interrupting, arresting or stopping their growth and metastases and does not necessarily indicate a total elimination of the tumor cell or neoplasm.

A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutcially effective amount of a compound of formulae (I) or (II) is expected to vary from about 0.1 milligram per kilogram of body weight per day (mg/kg/day) to about 30 mg/kg/day. For the treatment of a patient (70 kg), in early phases an intravenous infusion treatment of at most 1200 mg per day and in the later rehabilitation phase an oral administration of 3 times 300 mg per day of the compound of the formula I or II and/or of the corresponding salts of the compound of the formula II are indicated.

Under certain circumstances, however, even higher or lower doses may be appropriate. The dose can be administered both by single administration in the form of an individual dose unit or else of several smaller dose units and by multiple administration of subdivided doses at certain intervals.

Finally, the compounds of the formula I or II and/or their corresponding salts can also be combined together with other suitable active compounds, for example antiuricopathics, platelet aggregation inhibitors, analgesics and steroidal or nonsteroidal antiinflammatories, during the preparation of the abovementioned pharmaceutical administration forms.

EXAMPLE 1
N-(4-Trifluoromethylphenyl)-2-cyano-3-hydroxyhept-2-en-6-yne-carboxamide sodium salt (compound 1)

50 g (0.15 mol) of N-(4-trifluoromethylphenyl)-2-cyano-3-hydroxyhept-2-en-6-ynecarboxamide are dissolved in a two-phase system of 50 ml of 5 N sodium hydroxide solution and 500 ml of ethyl acetate, and the organic phase is separated off, washed twice with a little water, dried over sodium sulfate and concentrated. The oily residue is taken up using 500 ml of tertiary-butyl methyl ether and stirred at room temperature for 4 hours (h) to complete crystallization, filtered and dried under reduced pressure. For the complete removal of solvent residues, the crystalline product is suspended under reflux for 10 min in 500 ml of toluene, cooled with stirring, filtered off with suction again and dried under reduced pressure. Yield: 41.1 g (77%) of melting point >244° C. decomposition (dec.). $C_{15}H_{10}F_3N_2O_2Na$ (330.24 g/mol):

| calculated | C: 54.0 | H: 3.5 | N:8.4 | Na: 6.88 | (calc. for 1.1% water) |
| found | C: 54.4 | H: 3.4 | N:8.4 | Na: 6.65 | water: 1.1% |

EXAMPLE 2
2-Cyano-3-cyclopropyl-3-hydroxyacrylic acid (4-cyanophenyl)amide sodium salt (compound 2)

15 g (0.059 mol) of 2-cyano-3-cyclopropyl-3-hydroxyacrylic acid (4-cyanophenyl)amide are suspended in 120 ml of water and 100 ml of acetone and brought into solution by addition of 60 ml of 1N NaOH. After filtration of traces of undissolved material, the solution is concentrated under reduced pressure in a rotary evaporator to approximately 200 ml, and the product is crystallized overnight at 0° C., filtered off with suction and dried under reduced pressure.

Yield: 13 g, m.p. >280° C. $C_{14}H_{10}N_3O_2Na$ (275.24):

| calculated | C: 60.7 | H: 3.7 | N:15.2 | (calc. for 0.7% water) |
| found | C: 60.8 | H: 3.6 | N:15.3 | water: 0.7% |

EXAMPLE 3
N-(4-Trifluoromethylphenyl)-2-cyano-3-hydroxyhept-2-en-6-ynecarboxamide lysine salt 30 g (0.097 mol) of N-(4-trifluoromethylphenyl)-2-cyano-3-hydroxy-hept-2-en-6-ynecarboxamide are dissolved in 1 l of water and 25 ml of ethanol together with 17.3 g (0.097 mol) of L-lysine hydrate, filtered and lyophilized. Adhering residual amounts of ethanol are removed by repeated freeze drying.

Yield: 44.4 g of mainly amorphous product, m.p. 135–138° C. $^1$H-NMR (DMSO-$d_6$): 1.23–1.77 (m, 6H), 2.3–2.45 (m, 2H), 2.50–2.65 (m, 2H), 2.7–2.85 (m, 3H), 3.25 (tb, 1H), 5.7–7.4 (sb, 6H), 7.55 and 7.73 (AA'BB', in each case 2H), 12.35 (s, 1 H)

EXAMPLE 4
2-Cyano-3-cyclopropyl-3-hydroxyacrylic acid (4-cyanophenyl)amide lysine salt 15 g (0.054 mol) of 2-cyano-3-cyclopropyl-3-hydroxyacrylic acid (4-cyanophenyl)amide are dissolved in 900 ml of water and 10 ml of ethanol together with 9.6 g (0.054 mol) of L-lysine hydrate, filtered and lyophilized. Adhering residual amounts of ethanol are removed by drying under reduced pressure.

Yield: 21.8 g of mainly amorphous product, m.p.>100° C. (dec.). $^1$H-NMR (DMSO-$d_6$): 0.6–0.82 (m, 4H), 1.27–1.75 (m, 6H), 2.17 (mc, 1H), 2.77 (tb, 2H), 3.28 (tb, 1H), 4.8–7.5 (sb, 6H), 7.63 and 7.7 (AA'BB', in each case 2H), 12.6 (s, 1H)

EXAMPLE 5
Human DHODH (spleen) enzyme activity is determined according to Williamson et al. (The Journal of Biological Chemistry, 270, (1995), pages 22467–22472). The $IC_{50}$ value is in each case given in nM.

TABLE 1

| | DHODH $IC_{50}$ in nM |
|---|---|
| Compound 1 | 292 |
| Compound 2 | 625 |
| Compound 12 | 539 |
| Brequinar | 4 |

EXAMPLE 6
Inhibition of the proliferation of tumor cells (MTT test)

$1\times10^4$ cells per well are inoculated into a 96-well microtiter plate. After 24 h, the test substances are added at various concentrations. Each group consists of 4 wells, the control is only incubated with medium. After 65 h, 50 µl of MTT (3-(4,5-dimethyl-2-thiazolyl)-2,5-diphenyl-2H-tetrazolium bromide; 2.5 mg/ml in PBS) are added and, after 7 h, the supernatant is removed. The color formed by the living cells is dissolved by addition of 100 µl of dimethyl sulfoxide/well. The extinction is measured at 492 nm for each well with the aid of a Multiscan photometer 340 CC (Flow). The cell lines used are obtainable as follows from the American Type Culture Collection: HUV-EC-C is ATCC CRL 1730; A-172 is ATCC CRL 1620; L 1210 is ATCC CCL 219; LoVo is ATCC CCL 229; C 6 is ATCC CCL 107 and a rat glioblastoma cell line.

The mean value is formed from the 4 wells of a group and the $IC_{50}$ values are calculated from the dose-response curve using the Software 3.0 (Erithacus Software Ltd.). Table 2 shows the results.

TABLE 2

MTT Test
IC$_{50}$ in µM

| Cell | Origin (human) | Compound 1 | Compound 2 | Brequinar |
|---|---|---|---|---|
| LoVo | Colonic carcinoma | 137 | 392 | 0.388 |
| HUV-EC-C | Endothelial cell | 164 | 360 | 9.4 |
| A-172 | Glioblastoma | 78 | 169 | 0.2 |
| L1210 | Leukemia(mouse) | 9.1 | 6.1 | 1.0 |
| C6 | Rat glioblastoma | 68 | 20 | 9 |

EXAMPLE 7

The procedure is as in Example 6; uridine is additionally added to the batches. Table 3 shows the results.

TABLE 3

MTT Test on LoVo cells
IC$_{50}$ in µM

| Uridine [µM] | Compound 1 | Compound 2 | Brequinar |
|---|---|---|---|
| 0 | 168.0 | 359.2 | 0.388 |
| 1000 | 277.7 | 560.0 | 128.8 |

The compounds mentioned in Table 4 are prepared as in Examples 1 to 4. The compounds are tested as described in Example 6.

| Compound | Structure | A172 | C 6 | LoVo | HUVEC |
|---|---|---|---|---|---|
| 1 | 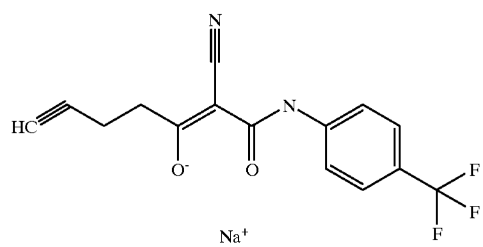 | 78 | 68 | 137 | 164 |
| 2 | 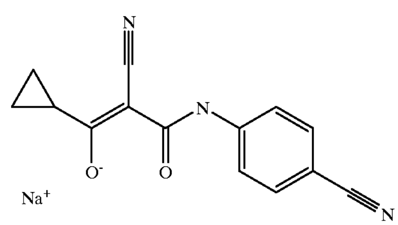 | 169 | 20 | 392 | 360 |
| 5 | 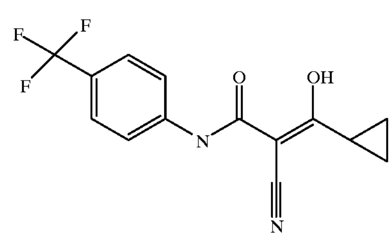 | 30 | 5 | 34 | 94 |
| 6 | 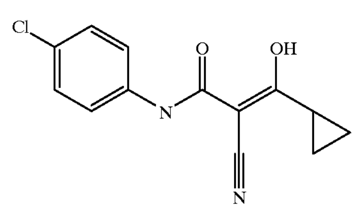 | 25 | 11 | 24 | >400 |

-continued
| Compound | Structure | A172 | C 6 | LoVo | HUVEC |
|---|---|---|---|---|---|
| 7 | 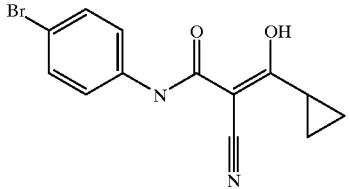 | 37 | 11 | 37 | 267 |
| 8 | 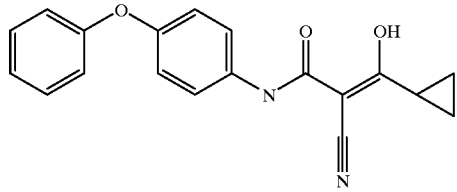 | 28 | 18 | 13 | 138 |
| 9 | 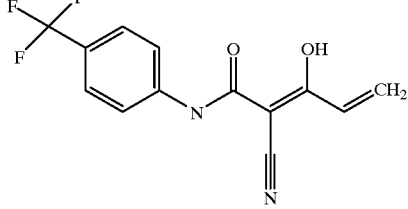 | 193 | 21 | 400 | >400 |
| 10 | 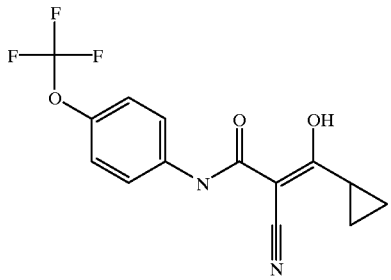 | 25 | 4 | 21 | 186 |
| 11 | 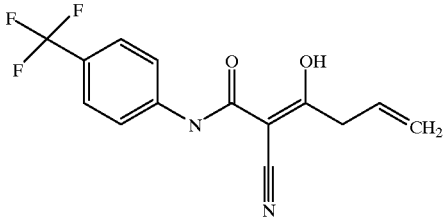 | 55 | 57 | 160 | 187 |
| 12 | 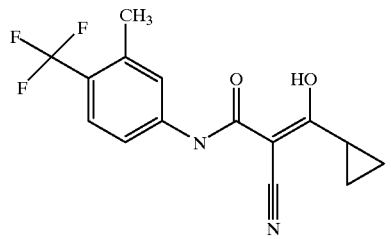 | 43 | 6 | 55 | 322 |

-continued
| Compound | Structure | A172 | C 6 | LoVo | HUVEC |
|---|---|---|---|---|---|
| 13 | 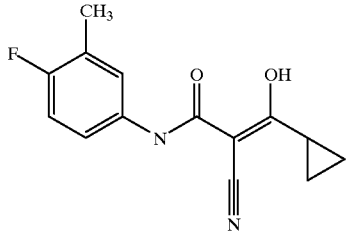 | 32 | 13 | 15 | >400 |
| 14 | 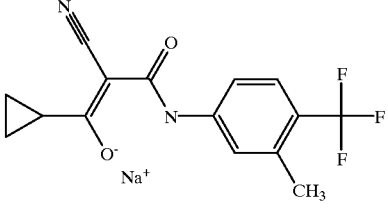 | 58 | 7 | 61 | 197 |
| 15 | 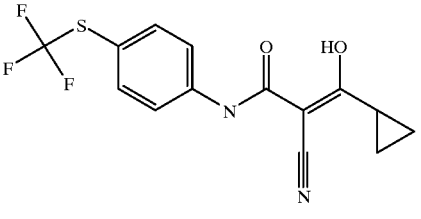 | 13 | 2 | 21 | 98 |
| 16 | 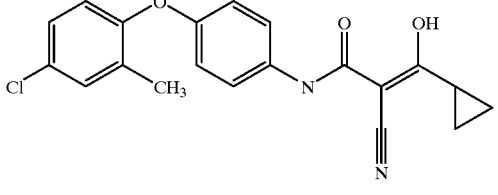 | 17 | 36 | 7 | 299 |
| 17 | 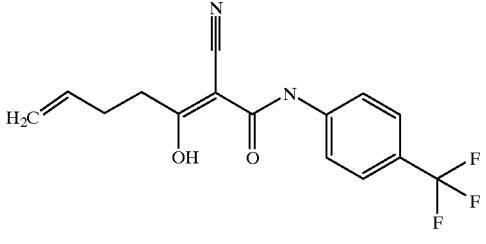 | 55 | 186 | 75 | 127 |
| 18 | 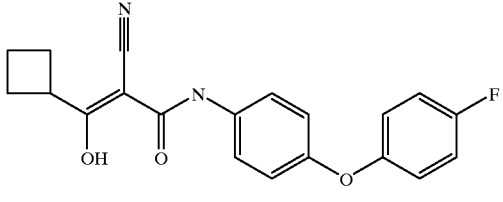 | 190 | 84 | 110 | 159 |

-continued

| Compound | Structure | A172 | C 6 | LoVo | HUVEC |
|---|---|---|---|---|---|
| 19 | 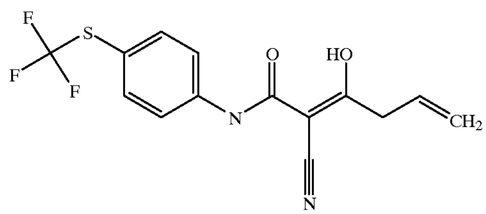 | 118 | 32 | 171 | 135 |
| 20 | 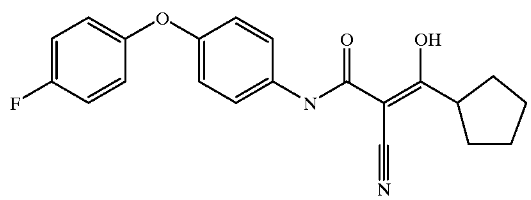 | 158 | 182 | 119 | >400 |
| 21 | 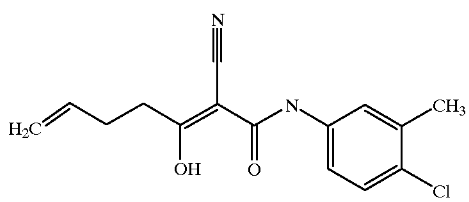 | 63 | 69 | 27 | 339 |
| 22 | 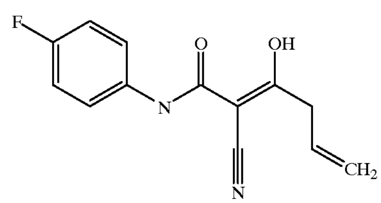 | >400 | 103 | 149 | >400 |
| 23 | 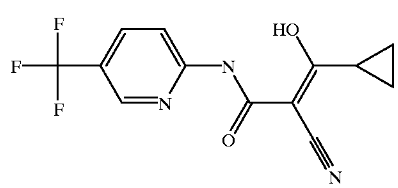 | 94 | 7 | 75 | >400 |
| 24 | 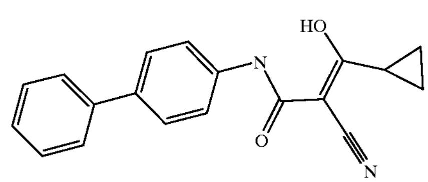 | 22 | 34 | 6 | 74 |
| 25 | 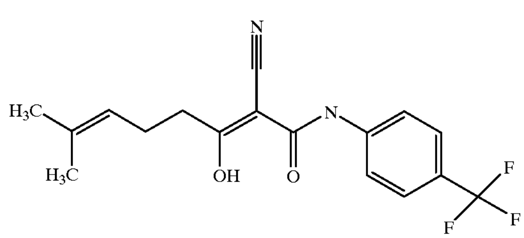 | 95 | 87 | 306 | 301 |

-continued

| Compound | Structure | A172 | C 6 | LoVo | HUVEC |
|---|---|---|---|---|---|
| 26 | 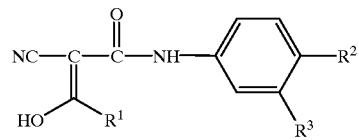 | 200 | 24 | 146 | 378 |
| 27 | 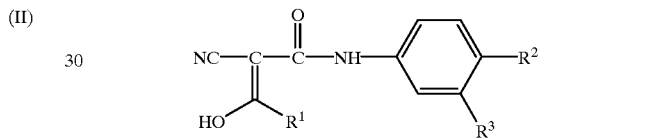 | 142 | 126 | 153 | >400 |

We claim:

1. A compound of the formula II (II)

wherein said compound is a lysine salt of the formula II; and wherein $R^1$ is
  a) $(C_3-C_5)$-cycloalkyl,
  b) $(C_2-C_6)$-alkenyl, or
  c) $(C_2-C_6)$-alkynyl;

$R^2$ is
  a) —$CF_3$,
  b) —O—$CF_3$,
  c) —S—$CF_3$,
  d) —OH,
  e) —$NO_2$,
  f) halogen,
  g) benzyl,
  h) phenyl,
  i) —CN,
  j) —O—phenyl, or
  k) —O—phenyl, mono-, or polysubstituted by
     1) $(C_1-C_4)$-alkyl,
     2) halogen,
     3) —O—$CF_3$, or
     4) —O—$CH_3$;

$R_3$ is
  a) $(C_1-C_4)$-alkyl,
  b) halogen, or
  c) a hydrogen atom; and

X is
  a) a —CH group, or
  b) a nitrogen atom.

2. A compound of the formula II (II)

wherein said compound is a sodium salt of the formula II; and wherein $R^1$ is
  a) $(C_3-C_5)$-cycloalkyl,
  b) $(C_2-C_6)$-alkenyl, or
  c) $(C_2-C_6)$-alkynyl;

$R^2$ is
  a) —$CF_3$,
  b) —O—$CF_3$,
  c) —S—$CF_3$,
  d) —OH,
  e) —$NO_2$,
  f) halogen,
  g) benzyl,
  h) phenyl,
  i) —CN,
  j) —O—phenyl, or
  k) —O—phenyl, mono-, or polysubstituted by
     1) $(C_1-C_4)$-alkyl,
     2) halogen,
     3) —O—$CF_3$ or
     4) —O—$CH_3$;

$R_3$ is
  a) $(C_1-C_4)$-alkyl,
  b) halogen, or
  c) a hydrogen atom, and

X is
- a) a —CH group, or
- b) a nitrogen atom.

3. A pharmaceutical composition comprising the compound of claim 1 and a pharmaceutically acceptable excipient.

4. A pharmaceutical composition comprising the compound of claim 2 and a pharmaceutically acceptable excipient.

* * * * *